United States Patent [19]

Leahey et al.

[11] 4,256,105

[45] Mar. 17, 1981

[54] EQUIPMENT SETS HAVING REDUCED DIAMETER PRIMARY TUBE FOR THE SEQUENTIAL ADMINISTRATION OF MEDICAL LIQUIDS AT DUAL FLOW RATES

[75] Inventors: John J. Leahey, Libertyville; Andrew J. Muetterties, Gages Lake; Joseph N. Genese, Waukegan, all of Ill.

[73] Assignee: Abbott Laboratories, North Chicago, Ill.

[21] Appl. No.: 16,267

[22] Filed: Feb. 28, 1979

[51] Int. Cl.³ .............................................. A61M 5/14
[52] U.S. Cl. ................................ 128/214 G; 128/227; 137/113; 222/145
[58] Field of Search ........... 128/214 R, 214 C, 214 G, 128/214.2, 227; 222/129.2, 145; 137/113

[56] References Cited

U.S. PATENT DOCUMENTS

| | | | |
|---|---|---|---|
| 3,177,870 | 4/1965 | Salem et al. | 128/214.2 |
| 3,217,711 | 11/1965 | Pecina et al. | 128/214 C |
| 3,886,937 | 6/1975 | Bobo et al. | 128/214 R |
| 4,034,754 | 7/1977 | Virag | 128/214 G |
| 4,078,563 | 3/1978 | Tuseth | 128/214 C |
| 4,116,646 | 9/1978 | Edwards | 55/159 |

*Primary Examiner*—Dalton L. Truluck
*Attorney, Agent, or Firm*—Robert S. Beiser; Robert L. Niblack

[57] ABSTRACT

Equipment sets for the sequential administration of medical liquids wherein a primary liquid can be administered at a flow rate independent of the flow rate of a secondary liquid, and including a barrier substantially impervious to air to prevent the inadvertent administration of air when the secondary liquid is depleted. The sets of this invention have a tube of reduced diameter to restrict the flow of primary liquid to a predetermined rate.

20 Claims, 4 Drawing Figures

EQUIPMENT SETS HAVING REDUCED DIAMETER PRIMARY TUBE FOR THE SEQUENTIAL ADMINISTRATION OF MEDICAL LIQUIDS AT DUAL FLOW RATES

BACKGROUND OF THE INVENTION

The present invention relates to systems and equipment sets for the administration of medical liquids to a patient, and more particularly, to systems and equipment sets for the sequential administration of a plurality of medical liquids.

The parenteral administration of medical liquids to patients is a long established practice. Liquids including amino acids, blood, dextrose, electrolytes, and saline are commonly administered to patients over prolonged periods of time. Generally, these liquids are administered from a glass bottle or plastic bag suspended above the patient and containing 250–2,000 ml. of the liquid. Such prolonged infusions commonly are administered at a flow rate of 10–150 ml./hr.

Frequently, the patient must receive an additiveor secondary liquid while the prolonged infusion is being administered. Preferably, this secondary liquid should be administered through the same hypodermic needle to avoid unnecessary pain and trauma to the patient of additional venipunctures. To avoid dilution and incompatability problems, it is also preferable that the flow of the primary liquid employed in the prolonged infusion be temporarily interrupted, the secondary liquid administered and the flow of the primary liquid resumed. Generally, the secondary liquid will be administered at a flow rate of 50–250 ml./hr.

Abbott Laboratories, North Chicago, Illinois manufactures a y-type set for the sequential administration of primary and secondary liquids. These VENOSET piggyback sets allow the prolonged infusion of a primary liquid to be temporarily halted by means of a backcheck valve in the primary liquid flow path to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al., assigned to American Hospital Supply Corp., and entitled "Medical Administration Set for Dispensing Plural Medical Liquids". Another similar system is disclosed in U.S. Pat. No. 4,105,029 granted Aug. 8, 1978 to R. Virag, assigned to Baxter Travenol and entitled "Intravenous Solution Set Having An Air Access Site and Constricted Inner Diameter Portion".

An inherent disadvantage of the above-mentioned prior art medical liquid administration systems is that they each resume the flow of primary liquid at the rate the secondary liquid had been flowing. Because the preferred flow rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary liquid flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Accordingly, it will be apparent that an efficacious system for the sequential administration of medical liquids at dual flow rates would be advantageous to the medical profession.

SUMMARY OF THE INVENTION

The primary object of the present invention, therefore, is to provide an equipment set for the sequential administration of medical liquids at dual flow rates that will not draw air from the secondary container when the secondary liquid has been depleted.

In accordance with this and other objects, there is provided by the present invention an equipment set for the sequential administration of medical liquids to a patient including a primary tube, a secondary tube, and a common tube all connected in fluid communication to form a primary liquid flow path and a secondary liquid flow path. The primary liquid flow path includes the primary and common tube, while the secondary liquid flow path includes the secondary and common tubes.

The primary tube includes a primary valve which allows primary liquid to flow from a primary liquid container whenever the height of primary liquid is greater than or equal to the height of the secondary liquid in the system. The primary valve, which can be a backcheck valve, prevents primary liquid from flowing out of the primary container whenever the height of the primary liquid is less than the height of secondary liquid in the system.

To establish the dual flow rates of the primary and secondary liquids, a secondary flow control means is provided in the secondary liquid flow path for adjusting the flow rate of the secondary liquid, while a portion of the primary tube has a reduced diameter for adjusting the flow rate of the primary liquid to a predetermined rate greater than, less than, or equal to the flow rate of the secondary liquid, (primary flow control means). An air barrier in the secondary liquid flow path that is substantially impervious to air is provided to insure that no air is drawn from the secondary container when the secondary liquid is depleted.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein.

DETAILED DESCRIPTION OF THE INVENTION

Figure 1:
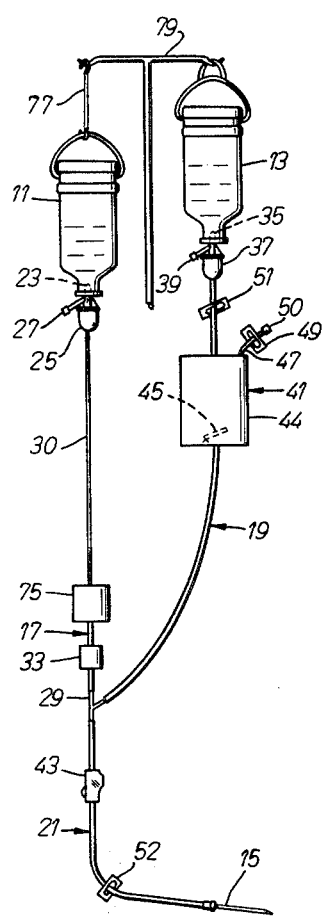
FIG. 1 is a front elevational view of one embodiment of the efficacious equipment sets for the sequential administration of medical liquids at dual flow rates contemplated by this invention.
Figure 2:
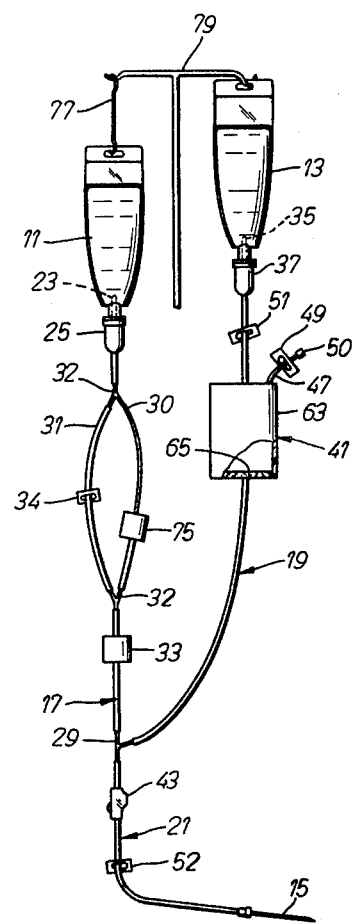
FIG. 2 is a front elevational view of another embodiment of the equipment sets contemplated by this invention.

Referring to the drawing, there is shown in FIGS. 1 and 2, two embodiments of the basic elements of the equipment sets for the sequential administration of medical liquids at dual flow rates contemplated by this invention.

The FIGS. depict a primary liquid container 11 that contains a primary medical liquid to be administered to a patient for a prolonged period of time. The FIGS. also depict a secondary liquid container 13 that contains a secondary medical liquid to be administered to the patient for a relatively short period of time, during which time the administration of the primary liquid will be temporarily interrupted. As shown in the sets of FIGS. 1 and 2, respectively, containers 11 and 13 can be glass bottles, plastic flexible bags, or any other suitable container.

Primary container 11 and secondary container 13 are connected in fluid communication to a conventional hypodermic needle 15 through a primary tube 17, a secondary tube 19, and a common tube 21. Thus, the primary liquid flow path from primary container 11 to needle 15 comprises primary tube 17 and common tube 21. Likewise, the secondary liquid flow path from secondary container 13 to needle 15 comprises secondary tube 19 and common tube 21.

The distal end of primary tube 17 is in fluid communication with primary container 11, preferably by means of a piercing pin 23 inserted into a puncturable closure of container 11. Piercing pin 23 can have an integral drip chamber 25, and when container 11 is a glass bottle, as shown in the set of FIG. 1, an integral, filtered air vent 27. such piercing pins, drip chambers and air vents are well known in the medical practice and need not be more fully explained here.

The proximal end of primary tube 17 is joined in fluid communication to the distal end of common tube 21, preferably by a y-tube 29, it being understood that the primary, secondary and common legs of y-tube 29 constitute a portion of the primary, secondary and common tubes 17, 19 and 21, respectively. As shown in FIGS. 1 and 2, primary tube 17 has a portion 30 having a constricted or reduced inner diameter for restricting the flow of primary liquid through primary tube 17 to a predetermined rate portion 30 thus serves as a primary flow control mechanism. As shown in FIG. 2, primary tube 17 also includes a portion 31 joined in parallel to constricted portion 30 by y-tubes 32. Portion 31 has a substantially larger inner diameter than reduced portion 30 and, accordingly, does not affect the flow rate of primary liquid through primary tube 17. Portion 31 has slide clamp 34 that prevents or permits primary liquid to flow through portion 31.

Figure 3:
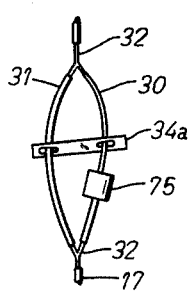
FIG. 3 is a front elevational view of an alternate version of part of the set of FIG. 2.
Figure 4:
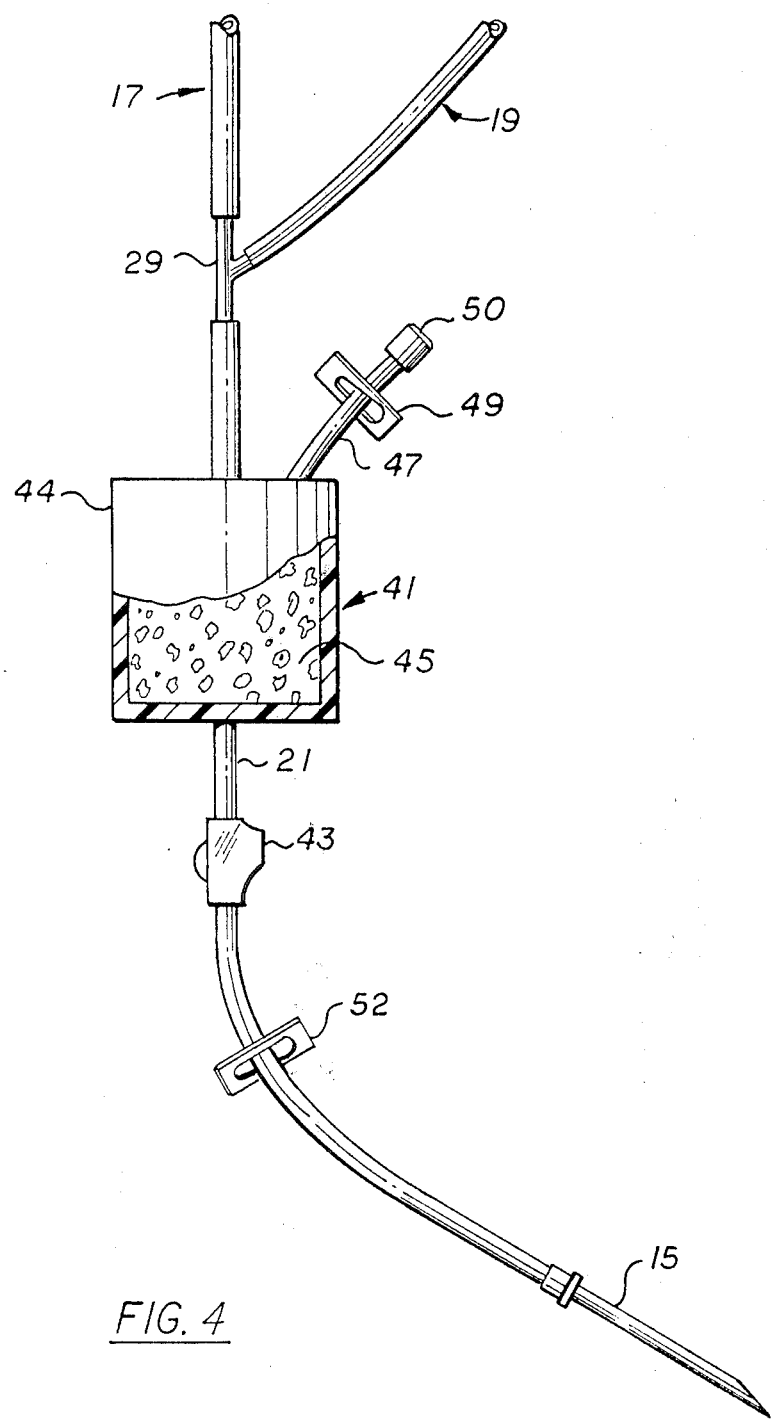
FIG. 4 of the drawings is a front view partially broken away of a medical liquid administration set embodying the system of FIG. 1, with an air filter in the common tube of the set.

Alternativey, as shown in FIG. 3, portions 30 and 31 can be provided with a common clamp 34a. Clamp 34a is designed so that when it is slid to open constricted portion 30, portion 31 will be closed and vice versa.

Primary tube 17 includes a primary valve 33 between its proximal end and reduced portion 30. Primary valve 33 allows primary liquid to flow from primary container 11 whenever the height of the primary liquid is greater than or equal to the height of the secondary liquid in the system. Further, primary valve 33 prevents the flow of primary liquid from primary container 11 whenever the height of the primary liquid is less than the height of the secondary liquid in the system.

While primary valve 33 has been shown in the sets of FIGS. 1 and 2 as being spaced from the proximal end of primary tube 17, it will be readily apparent that primary valve 33 can be incorporated into the primary leg of y-tube 29, if so desired. For example, primary valve 33 can be a conventional, one-way, backcheck valve mounted within the primary leg of y-tube 29.

The distal end of secondary tube 19 is in fluid communication with secondary container 13, preferably, by means of a piercing pin 35 inserted into a puncturable closure of container 13. Piercing pin 35 can have an integral drip chamber 37, and when container 13 is a glass bottle, as shown in FIG. 1, an integral, filtered air vent 39. The proximal end of secondary tube 19 is joined in fluid communication to the distal end of common tube 21, preferably, by a y-tube 29.

An air barrier 41 and flow control device 43 are located in the secondary liquid flow path. Preferably, as shown in FIGS. 1 and 2, secondary flow control 43 can be a roller clamp. However, it can be any other adjustable device that can reliably maintain a desired secondary liquid flow rate.

As shown in FIGS. 1 and 2, air barrier 41 is located in secondary tube 19, which is its preferred location. However, air barrier 41 can be located in common tube 21, if so desired. Likewise, for increased reliability of the system, a plurality of air barriers 41 can be located in either the secondary tube 19, common tube 21, or both. Further, while air barrier 41 is shown spaced from the proximal end of secondary tube 19, it will be readily apparent that air barrier 41 can be incorporated into the secondary or common tube legs of y-tube 29.

The air barrier 41 shown in the set of FIG. 1 comprises a housing 44 that has an inlet and outlet in fluid communication with secondary tube 19 and constitutes a portion of it. The outlet from housing 44 has a float valve 45 which floats away from the outlet when liquid is present in housing 44, but seats or closes over the outlet when no liquid is present. It will be apparent to those skilled in the art that numerous other conventional mechanical valves can be employed to perform the function of float valve 45, so long as the valve forms a barrier impermeable by air when no liquid is present in the housing 44.

The housing of the sets shown in FIGS. 1 and 2 each include an air vent tube 47 having a slide clamp 49 and a filtered opening 50. Alternatively, opening 50 can be filtered by a hydrophobic membrane filter which is permeable by air, but not liquids. The hydrophobic filters can be formed of polyfluorotetraethylene, hexafluoropropylene/tetrafluoroethylene copolymer, or other suitable materials. One such filter is made of Gelman ANH-450 material made by Gelman Instruments of Ann Arbor Michigan. When such a hydrophobic filter is used, slide clamp 49 can be eliminated.

The sets shown in FIGS. 1 and 2 include a slide clamp 51 near the distal end of secondary tube 19 and a slide clamp 52 near the proximal end of common tube 21.

As shown in the set of FIG. 2, air barrier 41 comprises a housing 63 having an inlet and outlet in fluid communication with secondary tube 19 and constitutes a portion of it. The outlet from housing 63 is covered by a hydrophilic membrane filter 65 which is impermeable to air when wet. The hydrophilic filter can be formed from materials such as a cellulose acetate material produced by the Millipore Filter corporation of Bedford, Massachusetts or the Sartorius-Membranfilter GmbH of Weender Landstr, West Germany.

Surprisingly, it has been found that with constricted portion 30 of primary tube 17 located on the distal side of primary valve 33, as shown in FIG. 1, certain embodiments of primary valve 33 might not remain closed as expected whenever the height of primary liquid is less than the height of secondary liquid in the system. The same result occurs in the sets of FIGS. 2 and 3 when clamp 34 or 34a is positioned to prevent the flow of liquid through portion 31. This unexpected opening results from the reaction force on primary valve 33 caused by primary liquid that cannot flow upwardly past constricted portion 30 when primary valve 33 initially closes. This reaction force reopens valve 33 and keeps it open.

It has been found that this unexpected opening of primary valve 33 can be obviated by the inclusion in primary tube 17 of a chamber 75 for a compressible mass. As shown in FIGS. 1 and 2, chamber 75 is located between constricted portion 30 and primary valve 33 and provides a cushion or spring for relieving pressures on the distal side of primary valve 33 whenever valve 33 closes in response to the height of primary liquid being less than the height of secondary liquid in the system. Although primary valve 33 and chamber 75 are shown as separate units, it will be apparent that they can be combined into one unit, if so desired.

As shown in the sets of FIGS. 1 and 2, chamber 75 has a housing with an inlet and outlet in fluid communication with primary tube 17. However, it is contemplated that chamber 75 can have only one opening in communication with primary tube 17. That is, chamber 75 may have a single opening transverse to the normal flow of liquid through primary tube 17 so that primary liquid only flows in or out of its single opening when reverse flow pressures exist on the distal side of primary valve 33.

Generally, the compressible mass of chamber 75 will be air and its housing will be a rigid opaque plastic. However, it is contemplated that the compressible mass of chamber 75 can be a sponge or other flexible solid materials, as well. Further, the housing of chamber 75 can be a flexible material which is compressible by the primary liquid to expand chamber 75, if so desired.

For simplicity, the equipment sets of this invention have been depicted and described as integral units in FIGS. 1 and 2. It is apparent, however, that the sets can be manufactured and assembled in subsets of the entire set and that each subset will accordingly be provided such resealable closures, piercing means, adapters etc. as are necessary to permit their easy assemblage into the complete set at an appropriate time. It will also be apparent that each of the several components of the sets of FIGS. 1 and 2 can be interchanged or combined in combinations other than those specifically depicted.

OPERATION OF THE SYSTEM

As depicted in FIGS. 1 and 2, primary container 11 is suspended in space at a height above the patient by means of a hook 77 and stand 79. It will be apparent that other means for suspending the containers of this invention are well known.

To insure that all the air that might be forced into the patient has been removed from the set, the set is initially primed by first closing slide clamps 49, 51 and 52. If present, slide clamp 34 is slid to open portion 31 of primary tube 17, or slide clamp 34a is slid to open both portions 30 and 31. Piercing pin 23 is then inserted into the resealable closure of primary container 11. Flow control 43 is fully opened. Slide clamp 52 is is opened to allow primary liquid to flow through the primary liquid flow path and force all the air therefrom that might be forced into the patient. If chamber 75 is present in primary tube 17, a substantial volume of air will remain therein. Slide clamp 52 is then closed.

Clamp 49 on air vent 47 of air barrier 41 is then opened to allow primary liquid to flow into, or backprime, secondary flow path 19 and force all the air from air barrier 41. Slide clamp 49 is then closed. Alternatively, if the set is fully assembled, slide clamp 51 can be opened to allow primary liquid to force air out of the entire secondary tube 19. Slide clamp 51 is then closed.

During the initial priming of secondary tube 19, it is advantageous to hold secondary tube 19 at a height well below primary container 11. When secondary tube 19 has been primed, it is secured in a convenient place until its subsequent use.

Common tube 21, which preferably has an adapter at its proximal end open to the flow of liquid therefrom, is next connected to needle 15, which will generally have been already inserted into a vein of the patient. Slide clamp 52 will then be opened to allow primary liquid to flow through the primary liquid flow path to the patient's vein. In the set of FIG. 1, flow control device 43 can be allowed to remain fully open, so that the flow rate of primary liquid through primary tube 17 will be determined solely by the constricted or reduced inner diameter of portion 30. Alternatively, or in the sets of FIGS. 2 or 3 whenever portion 31 is open to the flow of liquid therethrough, flow control 43 is then adjusted to a setting that will provide the desired flow rate for a prolonged infusion of primary liquid into the patient, generally 10–150 ml./hr. As is well known in the medical practice, that flow rate can be visually observed by viewing and counting drops passing through the primary drip chamber 25.

Subsequently, when it is desired to administer a secondary liquid to a patient, piercing pin 35 of secondary tube 19 is inserted into the resealable closure of secondary container 13. If any portion of secondary tube 19 has not already been primed, it can now be primed with secondary container 13 held at a height well below primary container 11, secondary tube slide clamp 51 opened, common tube slide clamp 52 closed and slide clamp 34 or 34a, if present, slid to open portion 31 of primary tube 17. Primary liquid then is allowed to flow into, or backprime, secondary tube 19 until all the air that can be forced into the patient has been expelled from secondary tube 19.

Secondary container 13 is then suspended in space from stand 79 at a height substantially greater than the height of primary container 11, thereby immediately causing primary valve 33 to close. Common tube slide clamp 52 is opened, slide clamp 34 or 34a, if present, slild to close portion 31 of primary tube 17, and flow control 43 is then adjusted to a desired flow rate, typically 50–250 ml./hr., for the secondary liquid, which will then flow until the secondary container 13 is depleted. It will be apparent that the initial liquid flowing from secondary tube 19 will be the primary liquid with which it was primed.

When the height of primary liquid in the sets of FIGS. 1 and 2, becomes greater than the height of the secondary liquid, primary valve 33 will immediately open and allow primary liquid to flow from the primary container at the predetermined flow rate obtainable through constricted portion 30 of primary tube 17. The primary flow rate is, thus, independent of the secondary flow rate. In those instances where it is less than or equal to the secondary flow rate, both primary and secondary liquid will flow through common tube 21, until air reaches air barrier 41 in the secondary tube. Then only primary liquid will enter common tube 21. Air barrier 41 then prevents air from being drawn into common tube 21 and eventually to the patient's vein.

When primary container 11 becomes depleted of primary liquid, the primary piercing pin 23 is merely removed therefrom and inserted into the resealable closure of a new primary container, which is then suspended in place of the previous container. If primary container 11 had become empty, it will be necessary to reprime the entire system as when the first primary container was administered.

When secondary container 13 becomes depleted of secondary liquid, it can be left empty until another secondary liquid is to be administered. When another secondary liquid is to be administered, the secondary piercing pin 35 is merely removed from secondary container 13 and inserted into a new secondary liquid container. The secondary tube 19 must then be back-primed, as when the first secondary container was administered.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

That which we claim is:

1. In a set for the sequential administration of medical liquids to a patient, said set including:
    a primary tube for the flow of a primary medical liquid therethrough and including a primary check valve for controlling the flow of liquid through said primary tube which preventing backflow of a liquid therethrough,
    a secondary tube for the flow of a secondary medical liquid therethrough,
    a common tube having its distal end in fluid communication with the proximal ends of said primary and secondary tube and its proximal end open for the flow of liquid therefrom to form a primary liquid flow path comprising said primary tube and said common tube and a secondary liquid flow path comprising said secondary tube and said common tube, and
    a flow control means in said secondary liquid flow path for adjusting the flow rate of liquid therethrough, the improvement which comprises:
    primary flow control means on said primary liquid flow path comprising a first portion of said primary tube located on the distal side of said primary valve and having a constricted inner diameter for restricting the flow rate of said primary liquid through said primary flow path to a predetermined rate independent of the flow rate of said secondary liquid through said secondary liquid flow path, and
    an air barrier means within said secondary liquid flow path substantially impervious to air but permitting liquid flow therethrough while said set is in use and preventing the flow of air therethrough after said secondary liquid has been depleted.

2. The set defined in claim 1, wherein said flow control means is on said common tube and said primary tube further includes a second portion in parallel to and having a substantially larger inner diameter than said first portion, said second portion having a flow control means thereon to regulate the flow of said primary liquid through said second portion.

3. The set defined in claim 1 or 2, wherein said air barrier comprises a hydrophilic membrane disposed in a housing having an inlet and outlet in fluid communication with said secondary liquid flow path.

4. The set defined in claim 1 or 2, wherein said air barrier comprises a mechanical valve disposed in a housing having an inlet and outlet in fluid communication with said secondary liquid flow path.

5. The set defined in claim 4, wherein said mechanical valve is a float valve.

6. The set defined in claim 1 or 2, wherein said air barrier is located between the ends of said secondary tube.

7. The set defined in claim 1 or 2, wherein said air barrier is located between the ends of said common tube.

8. The set defined in claim 3, wherein said housing includes an air vent.

9. The set defined in claim 4, wherein said housing includes an air vent.

10. The set defined in claim 8 or 9, wherein said air vent is covered by a hydrophobic membrane.

11. The set defined in claim 1, wherein said primary tube further includes a primary piercing pin at its distal end for insertion into a container for a primary medical liquid and a drip chamber for forming drops of said primary liquid.

12. The set defined in claim 11, wherein said secondary tube further includes a secondary piercing pin at its distal end for insertion into a container for a secondary medical liquid, and a drip chamber for forming drops of said secondary liquid.

13. The set defined in claim 11 or 12, wherein said piercing pins and drip chambers are integral.

14. The set defined in claim 11 or 12, wherein said piercing pins have integral air vents.

15. The set defined in claim 1 or 2, wherein said primary valve is further characterized as a one-way valve that allows said primary liquid to flow towards said common tube, but prevents the flow of said secondary liquid into said primary tube.

16. The set defined in claim 15 and further including a chamber for a compressible mass in fluid communication with said primary tube between said first portion and said primary valve to provide a spring for relieving pressures on said primary valve whenever the height of said primary liquid is less than the height of said secondary liquid in the system.

19. The set defined in claim 16 or 18, wherein said chamber has only one opening thereto.

20. The set defined in claim 16 or 18, wherein said chamber has an inlet and outlet in communication with said primary tube.

17. The set defined in claim 16, wherein said compressible mass is air.

18. In a set for the sequential administration of medical liquids to a patient, said set including:
- a primary tube for the flow of a primary medical liquid therethrough and including a primary valve for controlling the flow of liquid through said primary tube,
- a secondary tube for the flow of a secondary medical liquid therethrough;
- a common tube having its distal end in fluid communication with the proximal ends of said primary and secondary tube and its proximal end open for the flow of liquid therefrom to form a primary liquid flow path comprising said primary tube and said common tube and a secondary liquid flow path comprising said secondary tube and said common tube, and
- a flow control means in said secondary liquid flow path for adjusting the flow rate of liquid therethrough, the improvement which comprises:

primary flow control means on said primary liquid flow path comprising a first portion of said primary tube located on the distal side of said primary valve and having a constricted inner diameter for adjusting the flow rate of said primary liquid through said primary flow path to a predetermined rate independent of the flow rate of said secondary liquid through said secondary liquid flow path, and an air barrier in said secondary liquid flow path substantially impervious to air while said set is in use and preventing the flow of air therethrough, a chamber for a compressible mass in fluid communication with said primary tube between said first portion and said primary valve to provide a spring for relieving pressures on said primary valve whenever the height of said primary liquid is less than the height of said secondary liquid in the system.

* * * * *